United States Patent [19]
Vishwakarma et al.

[11] Patent Number: 5,683,861
[45] Date of Patent: *Nov. 4, 1997

[54] BENZOTRIAZOLE-BASED UV ABSORBERS AND PHOTOGRAPHIC ELEMENTS CONTAINING THEM

[75] Inventors: Lal C. Vishwakarma; Glenn M. Brown, both of Rochester, N.Y.

[73] Assignee: Eastman Kodak Company, Rochester, N.Y.

[*] Notice: The term of this patent shall not extend beyond the expiration date of Pat. No. 5,500,332.

[21] Appl. No.: 735,543

[22] Filed: Oct. 23, 1996

[51] Int. Cl.$^6$ ............... G03C 1/815; C08K 5/34; C07D 249/16; C07D 403/00
[52] U.S. Cl. ............... 430/512; 430/931; 524/91; 548/260; 548/261
[58] Field of Search ............... 430/512, 931; 524/91; 548/260, 261

[56] References Cited

U.S. PATENT DOCUMENTS

| | | | |
|---|---|---|---|
| 3,272,891 | 9/1966 | Peter et al. | 260/895 |
| 3,399,173 | 8/1968 | Heller et al. | 548/260 |
| 4,041,044 | 8/1977 | White | 260/308 |
| 4,141,903 | 2/1979 | Adler | 260/308 |
| 4,224,451 | 9/1980 | Roberts et al. | 548/260 |
| 4,316,033 | 2/1982 | Ching | 524/91 |
| 4,719,248 | 1/1988 | Bambury et al. | 523/108 |
| 4,780,541 | 10/1988 | Seino | 548/260 |
| 4,835,284 | 5/1989 | Seino | 548/259 |
| 4,943,637 | 7/1990 | Seino et al. | 548/260 |
| 5,262,541 | 11/1993 | Moshchitsky et al. | 548/260 |
| 5,385,815 | 1/1995 | Schofield et al. | 430/512 |
| 5,500,332 | 3/1996 | Vishwakarma et al. | 430/512 |

FOREIGN PATENT DOCUMENTS

| | | |
|---|---|---|
| 0 257 151 | 3/1988 | European Pat. Off. . |
| 1324897 | 3/1963 | France . |
| 1324898 | 3/1963 | France . |
| 1330378 | 5/1963 | France . |
| 960141 | 6/1964 | United Kingdom . |
| 981539 | 1/1965 | United Kingdom . |
| 991142 | 5/1965 | United Kingdom . |
| 991204 | 5/1965 | United Kingdom . |
| 991320 | 5/1965 | United Kingdom . |
| 991630 | 5/1965 | United Kingdom . |
| 90/09369 | 8/1990 | WIPO . |

*Primary Examiner*—Richard L. Schillling
*Attorney, Agent, or Firm*—Edith A. Rice

[57] ABSTRACT

An ultraviolet absorbing compound of formula (I) below, and photographic elements containing such a compound as an ultraviolet absorber:

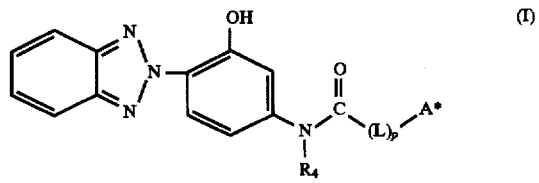

wherein:
- $R_4$ is a substituted alkyl group, $R_4$ may be further joined to either L or A* forming a ring and the benzo or phenyl ring shown may be further substituted or unsubstituted;
- L is a bivalent linking group;
- p is 0 or 1;
- A* is an alkyl group having an asymmetric carbon or asymmetric silicon atom, and;
- wherein the ultraviolet absorbing compound of formula (I) is a mixture of two enantiomers about the asymmetric carbon or silicon atom of A*.

25 Claims, 1 Drawing Sheet

BENZOTRIAZOLE-BASED UV ABSORBERS AND PHOTOGRAPHIC ELEMENTS CONTAINING THEM

FIELD OF THE INVENTION

This invention relates to particular benzotriazole based W absorbing compounds, and to photographic elements containing such compounds.

BACKGROUND

Typical photographic elements use silver halide emulsions, the silver halide having a native sensitivity to ultraviolet radiation. Ultraviolet radiation ("UV") as used in this application means light having a wavelength of 300–400 nm. Such UV sensitivity is usually undesirable in that it produces an image on the photographic element which is not visible to the human eye. Furthermore, the image dyes in the color photographs are known to fade due to action of UV light. Also other organic molecules such as unused color forming couplers in the emulsion layers and optical brighteners in the paper support degrade due to action of UV light and generate undesirable color stains on the finished photographs. Therefore, photographic elements typically contain a UV absorbing compound (sometimes referred to simply as a "UV absorber"). Another function of UV absorbers is to prevent the formation of undesirable patterns caused by electrostatic discharge in silver halide photographic materials. In general, IN absorbers impart light stability to organic molecules in various products which are susceptible to degrade as a result of the action of UV.

Generally, an effective UV absorber should have its peak absorption above a wavelength of 320 nm. The absorption peak may be at a longer wavelength, as long as absorption drops off sufficiently as it approaches the visual range (approximately 400 to 700 nm) so that no visible color is shown by the compound. In addition, to be effective, a UV absorber should have a high extinction coefficient in the desired wavelength range. However, for the most desirable UV protection, the high extinction coefficient should be at those wavelengths sufficiently below the visual range so that the compound should not be visually yellow.

UV absorbers of the benzotriazole class for photographic and other applications are well known. They include hydroxyphenyl benzotriazoles with various substituents on the hydroxyphenyl ring and also on the benzo ring. 2-Hydroxyphenyl benzotriazole UV absorbers with a large class of acylamino groups, including sec-amides, tert-amides, hydrazides, carbamates, sulfonamides, and many others, are described in FR 1,330,378, FR 1,324,898, FR 1,324,897, GB 991 204, GB 991 320, GB 991 142, Japanese Kokai JP 50-121178, WO 90/09369, U.S. Pat. No. 5,500,332 and GB 991 630.

UV absorbers which are currently used in photographic products include those of formula (II-A) and (II-B) below:

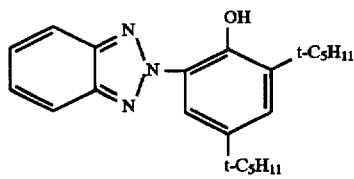

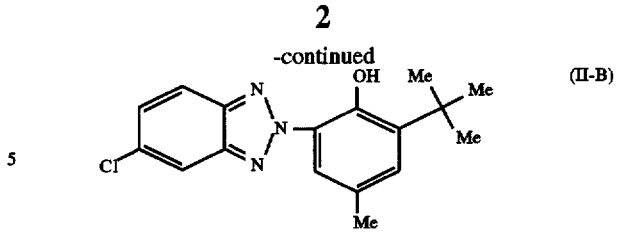

In the manufacture of photographic elements, UV absorbers usually are dissolved in a high boiling organic solvent and then dispersed in an aqueous medium containing a hydrophilic colloid, such as gelatin. Such dispersions are typically prepared up to about two weeks prior to use. It has been found that compounds (II-A) and (II-B) have a propensity to crystallize out during cold storage of a dispersion containing of them and that their intrinsic light stability is inferior.

Problem to be Solved by the Invention

It is therefore desirable to have UV absorbing compounds suitable for photographic uses, which are relatively stable in a photographic environment, and in particular have a low tendency to crystallize out at ordinary temperatures at which photographic elements are manufactured, used and/or stored, which have a higher extinction coefficient than that of (II-A)/(II-B)(collectively referred to herein as Comparative C-1), so that less of it needs to be used to obtain the same UV absorption, and which have a good UV absorption spectrum offering steeper slope and sharper drop-off at the longer wavelength side of the UV spectrum for photographic uses.

SUMMARY OF THE INVENTION

We have now discovered that benzotriazole-based UV absorbing compounds having tertiary-amide functional group containing an alkyl substituent having an asymmetric carbon or silicon atom eliminate crystal forming problem and offer superior intrinsic light stability.

One aspect of the present invention comprises an ultraviolet light absorbing compound of formula (I):

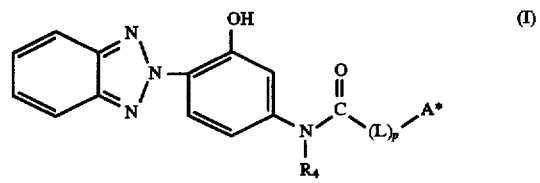

wherein:

$R_4$ is a substituted or unsubstituted alkyl group, or $R_4$ may be further joined to either L or A* forming a ring and the benzo or phenyl ring shown may be further substituted or unsubstituted;

L is a bivalent linking group;

p is 0 or 1;

A* is an alkyl group having an asymmetric carbon or asymmetric silicon atom, and wherein the ultraviolet absorbing compound of formula (I) is a mixture of two enantiomers about the asymmetric carbon or silicon atom of A*.

Another aspect of this invention comprises a photographic element containing an ultra violet absorbing compound of formula (I). UV absorbing compounds of formula (I) have a wavelength of maximum absorption ("λmax") which is desirable in the longer UV region (330–380 nm), have a sharp dropping absorption profile at wavelengths slightly shorter than 400 nm making them useful with known fluorescent brighteners, are relatively stable in the environment of a photographic element, do not readily crystallize in photographic elements, and have high extinction coefficients.

Most of the prior art W absorbers having an amide linkage with its tertiary-nitrogen atom directly attached to phenol ring either do not have an asymmetric carbon(s) containing alkyl substituent(s) or have an asymmetric carbon(s) containing alkyl substituent(s) but are lacking in tertiary nature of nitrogen atom of the amide linkage. Such compounds include, for example:

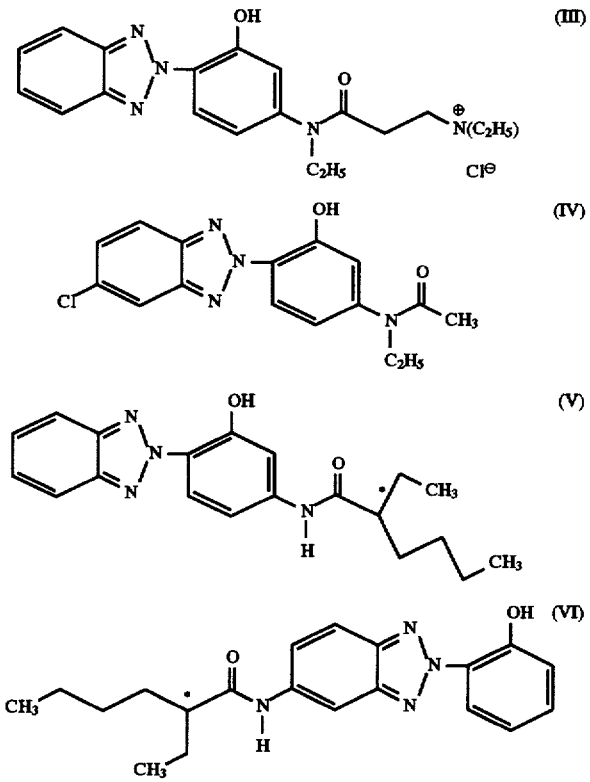

The problem with such UV absorbing compounds with amide groups as disclosed in the prior art is that these crystallize out when coated.

Advantageous Effect of the Invention

It has now been found that novel UV absorbers of the present invention have higher molar extinction coefficient, absorption spectrum has steeper slope and sharper drop-off on the longer wavelength side. Further, they have extremely high solubility in high-boiling hydrophobic organic solvents regardless of their physical state, have enhanced intrinsic light stability, and have no tendency of crystallization in dispersions or in photographic coatings and are therefore superior to the products of the state of the art in the photographic field. In some cases the UV absorbers are actually liquid and can be employed in a color photographic material without high boiling solvents.

DETAILED DESCRIPTION OF THE INVENTION

Figure 1:
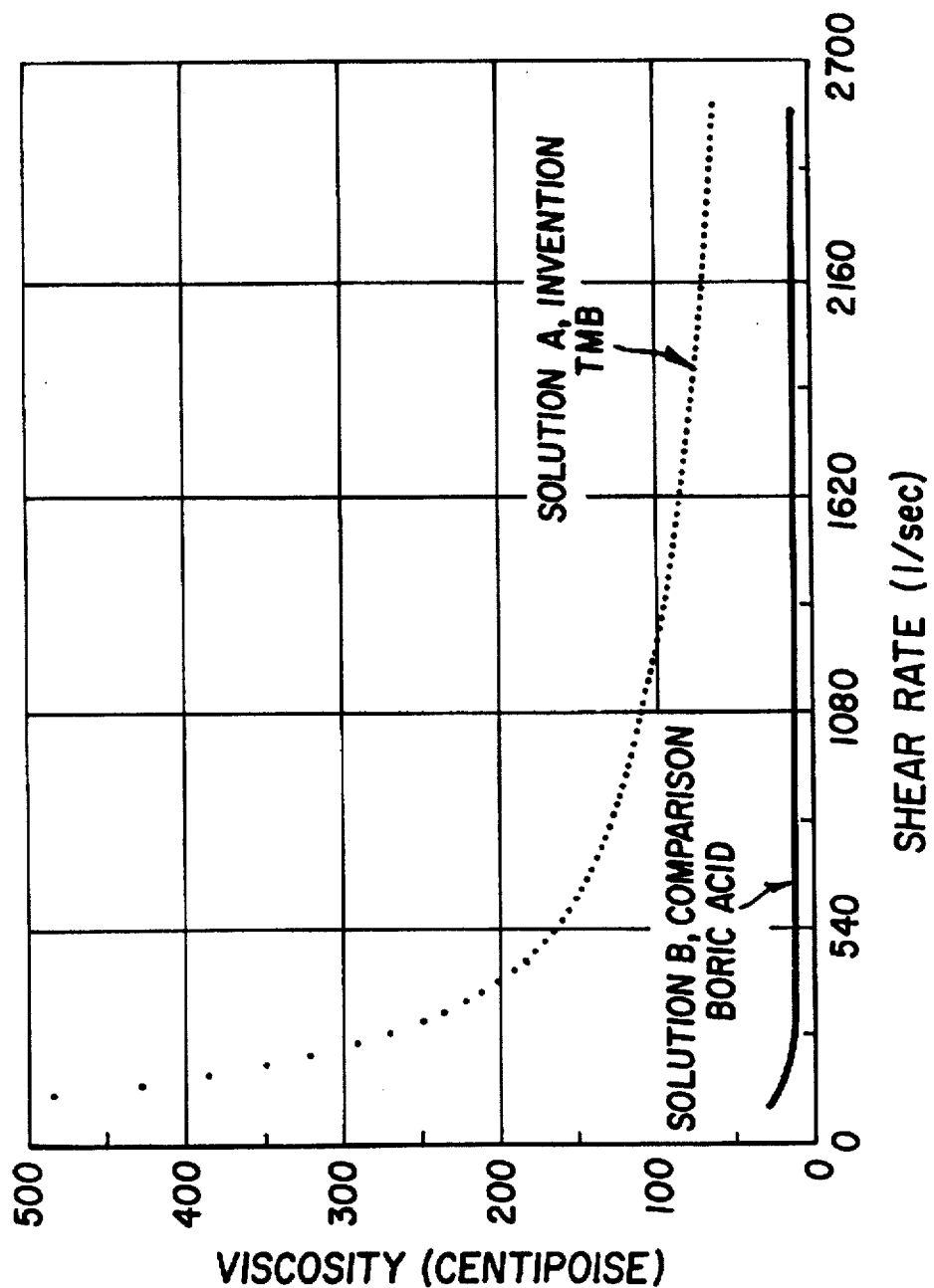
FIG. 1 shows the absorption spectra of coatings in a photographic element for an inventive compound I-1 (dashed line) and for a mixture of comparative compounds II-A and II-B, defined as C-1 (solid line), in total transmission mode illustrating higher extinction and sharper drop-off for I-1 at the longer wavelength side.

In the present application, reference to ultraviolet or UV in relation to the present invention refers to the wavelength range of 300 to 400 nm unless the contrary is indicated. Additionally, reference to "under", "above", "below", "upper", "lower" or the like terms in relation to layer structure of a photographic element, is meant the relative position in relation to light when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. Further, reference to any chemical "group" (such as alkyl group, aryl group, heteroaryl group, and the like) includes the possibility of it being both substituted or unsubstituted (for example, alkyl group and aryl group include substituted and unsubstituted alkyl and substituted and unsubstituted aryl, respectively). Generally, unless otherwise specifically stated, substituent Groups usable on molecules herein include any groups, whether substituted or unsubstituted, which do not destroy properties necessary for the photographic utility. It will also be understood throughout this application that reference to a compound of a particular General formula includes those compounds of other more specific formula which specific formula falls within the general formula definition.

As is well known, enantiomers have identical structural formulas except they are non-superimposable mirror images of one another. Further, in reference to enantiomeric mixtures, proportions are in mole ratios. When reference is made in this application to the ultraviolet absorbing compound of formula (I) being a mixture of two enantiomers about the asymmetric carbon or silicon of A*, this refers to a mixture of the two optical isomers about the racemic carbon or silicon of A* with R and S stereochemical configurations.

In compounds of formula (I), the bivalent linking group L may, for example, be an alkylene group having a chain of 1 to 20 atoms, preferably 1 to 10, more, preferably 1 to 6 and most preferably 1 to 3, in length, with or without up to 5 (or 2 or 1) intervening oxygen, sulfur or nitrogen atoms; an aryl group or a saturated or unsaturated heterocyclic group. However, when L is an alkylene group, it is preferred that the carbon atoms of L are all saturated. This means that none of the carbon atoms of L would have any type of carbon—carbon double or triple bonds. Thus, in this situation L would not have groups such as —C═C— or —C≡C—. The possibility of L having unsaturated atoms other than unsaturated carbon atoms, is not excluded. For example, L could be a group such as (A) below:

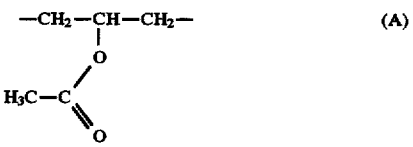

L may be unsubstituted or substituted with, for example, a 1 to 10 carbon alkoxy (or 1 to 6, or 1 to 2 carbon alkoxy), a 1 to 10 carbon atom alkyl sulfide (or 1 to 6, or 1 to 2 carbon alkyl sulfide), 0 to 10 carbon amino (or 0 to 6, or 0 to 2 carbon amino), or halogen. By L being substituted includes the possibility of the substituents forming a ring. For example, L can include an alicyclic or heterocylic ring (such as a 3 to 10 or 4, 5, or 6, membered ring). When the ring is heterocyclic it may contain, for example, have 1, 2, or 3 heteroatoms (which may be the same or different) selected from O, S or N. Examples of such rings as part of L include cyclohexyl, pyrrolidinyl, tetrahydrofuranyl, tetrahydrothienyl or piperidinyl, although less preferably such rings could also include benzo, pyrrolo, furyl, thienyl, pyridyl or spiroether containing rings. L may also include as a substituent, an ether or ester containing group. Particularly, the ether or ester containing substituent in L may be of the formula $R_8—O—(R_9)_n—$ or $R_8C(O)O—(R_9)_n—$, where $R_8$ and $R_9$ are, independently, an alkyl group and n is 0 or 1. $R_9$ may have, for example, 1 to 6 carbon atoms, while $R_8$ may have, for example, 1 to 20 carbon atoms (for example, 1 to 10, or 6 to 10).

The benzo ring and the hydroxy substituted phenyl ring may each be further substituted. For example, either may have 1 to 4 further substituents. Substituents may, for example, independently be, 1 to 18 carbon alkyl (or 1 to 6, or 1 to 2 carbon alkyl), aryl (such as 6 to 20 carbon atoms), heteroaryl (such as pyrrolo, furyl or thienyl), aryloxy (such as 6 to 20 carbon atoms) alkoxy (such as 1 to 6 or 1 to 2 carbon alkoxy), cyano, or halogen (for example F or Cl, particularly having Cl on the benzo ring at the 5-and/or 6-position, and/or on the hydroxy substituted phenyl at the 5'-position). Other substituents for the benzo ring can include: a ring fused thereto, such as a benzo, pyrrolo, furyl or thienyl rings; or $—N—CO—(L)_p—A^*$ in the 5- or 6-position of the benzene ring of the benzotriazole in which cases, the 4'-position of the hydroxyphenyl ring can be substituted with any of the substituents described herein for $R_1$ or $R_2$. Any of the alkyl and alkoxy substituents may have from 1 to 5 (or 1 to 2) intervening oxygen, sulfur or nitrogen atoms, including or not including asymmetric centers.

$R_4$ is an alkyl group, it may have, for example, from 1 to 20 C atoms (or 1 to 10 or 1 to 6 carbon atoms, such as methyl, ethyl, n-propyl or isopropyl, or butyl or pentyl either of which may be normal, secondary or tertiary). Substituents include alkoxy (particularly 1 to 6 carbon atoms), halogen (particularly Cl and F), and cyano. $R_4$ may be an electron withdrawing alkyl group such as perfluoroalkyl group.

When $R_4$ is not an electron withdrawing alkyl group, there may be a hypsochromic shift (shift to a shorter wavelength) in the wavelength of maximum UV absorption of a formula (I) compound. If desired, in such case the wavelength of maximum UV absorption may be again shifted longer by providing a substituent on the benzo ring of the benzotriazole, which has an unshared electron pair. Such substituents include Cl, F, dialkylamino, or an alkoxy. A 5'-alkyl group may also be used to correct the hypsochromic shift.

Electron withdrawing substituents in general, are discussed in March, Advanced Organic Chemistry, 3rd Ed., J. March, (John Wiley Sons, N.Y.; 1985) at pages 20–21, 228–229, 386–387, 494–497. In particular, preferred electron withdrawing substituents in each case described herein, or an electron withdrawing alkyl group for $R_4$, would have a Hammett $\sigma_p$ constant of greater than 0 (or greater than 0.1 or even 0.3) and preferably between 0.1 to 1.0 (for example, between any of 0.3, 0.4, 0.5 or 0.6 to 1.0). Hammett $\sigma_p$ values are discussed in the foregoing Advanced Organic Chemistry. Note that the "p" subscript refers to the fact that the σ values are measured with the substituents in the para position of a benzene ring. Additional tables relating to Hammett $\sigma_p$ constants can be found in Chemical Reviews Volume 91, pages 165–195 (authored by C. Hansch et al.).

As for A*, any alkyl group with an asymmetric carbon atom could be used. With the appropriate substituents on the asymmetric carbon, A* may have as little as only 1 carbon atom. The asymmetric carbon atom will preferably have at least three different alkyl groups, which means that A* will therefore preferably have at least 4 carbon atoms. A* may have 4 to 20 C atoms (or preferably 6 to 20 C atoms, 4 to 10 or 4 to 6 carbon atoms). A* is preferably of the structure $—CR_5R_6R_7$, as shown below in structure (Ia).

The compounds of formula (I) may particularly be of formula (Ia) below (some of carbon atoms on the rings being numbered in formula (Ia) to illustrate how the positions on the rings of benzotriazoles are identified in this application):

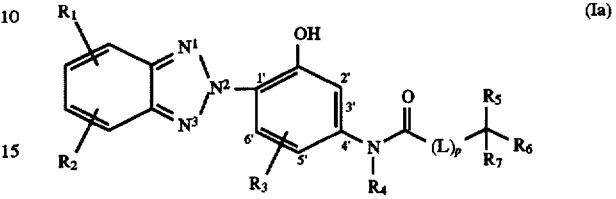

or more particularly of formula (Ib):

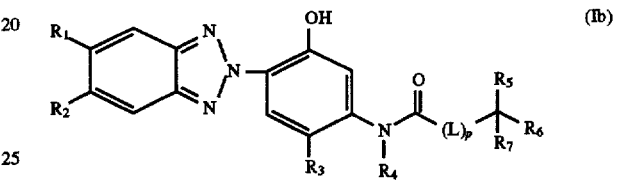

More particularly, in any of formulas (I), (Ia) or (Ib), $R_1$, $R_2$ and $R_3$ may be, independently, 1 to 18 (or 1 to 10, 1 to 6, or 1 to 2) carbon alkyl or alkoxy either of which may have 1–5 (or 1 or 2) intervening oxygen, sulfur or nitrogen atoms, or are aryl, heteroaryl, or aryloxy. $R_3$ may also be a 6'-hydroxy substituent. $R_1$, $R_2$ and $R_3$ may also be, independently any of the foregoing substituted with 1 to 17 (or 1 to 10, 1 to 6, or 1 or 2) carbon alkoxy, 1 to 17 (or 1 to 10, 1 to 6, or 1 or 2) carbon alkyl sulfide, 0 to 17 carbon amino (or 0 to 10, 0 to 6, or 0 to 2), or a halogen, or any of $R_1$, $R_2$ or $R_3$ may be H or a halogen (particularly chloro or fluoro) or both $R_1$ and $R_2$ together form a 5 to 18 carbon atom aryl group (such as a benzo ring) or heteroaryl ring group (for example, pyrrolo, furyl, thienyl, pyridyl). Substituents on the foregoing rings formed by $R_1$ and $R_2$ may include a 1 to 17 (or 1 to 10, 1 to 6, or 1 or 2) carbon atom alkyl or alkoxy, or a halogen.

$R_1$, $R_2$ and $R_3$ may also be, ndependently: a chloro; a fluoro; a hydroxy; a cyano; a carboxy; a carbalkoxy; a nitro; an acylamino group (for example, an acetylamino group), carbamoyl, sulfonyl, sulfamoyl, sulfonamido, acyloxy (for example, an acetoxy group or a benzoyloxy group), or an oxycarbonyl group (for example, a methoxycarbonyl group, etc.), any of which may have 1 to 18 (or 1 to 10, 1 to 6, or 1 to 2) carbon atoms. $R_4$ is as defined above.

Also, L may particularly have a total of 0 to 20 (or 0 to 10, or 0 to 4) atoms and be an alkylene group of which may have 1–5 (or 1, 2 or 3) intervening oxygen, sulfur or nitrogen atoms. Substituents on L include, for example, a 1 to 10 (or 1 to 6, or 1 or 2) carbon alkoxy, a 1 to 10 (or 1 to 6, or 1 or 2) carbon atom alkyl sulfide, 0 to 10 (or 0 to 6, or 0 to 2) carbon amino, or with halogen.

In the above formulas, $R_5$, $R_6$ and $R_7$ are, independently: H; halogen; cyano; an alkyl group or alkoxy group; thioalkyl group; alkylamino or arylamino group; an aryl group or aryloxy group; or a heteroaryl group. When any of $R_5$, $R_6$ and $R_7$ is an alkyl or alkoxy group it may, for example, have from 1 to 20 C atoms (or 1 to 10 or 1 to 6, such as methyl, ethyl, propyl, butyl or pentyl). Suitable aryl groups, aryloxy groups or heteroaryl groups may be selected from such groups as described in connection with $R_1$, $R_2$ and $R_3$ above.

Substituents on any of the foregoing groups for $R_5$, $R_6$ and $R_7$ may be selected from among the substituents on corresponding groups for $R_1$, $R_2$ and $R_3$ described above. Such substituents include alkoxy (particularly 1 to 6 carbon atoms), halogen (particularly Cl and F), and cyano. It is preferred that each of $R_5$, $R_6$ and $R_7$ is selected from H or alkyl groups.

It is important for the present invention that $R_5$, $R_6$ and $R_7$ be different such that the carbon or silicon atom bearing those groups is asymmetric (a racemic carbon or silicon center). However, the compound of formula (I) could have further racemic carbon centers. When $R_1$, $R_2$, $R_3$ or $R_4$ also contains an asymmetric carbon (or any other substituent also contains an asymmetric carbon), such that there are two or more asymmetric carbons in the compound, diastereomers can then be formed. This means that the UV absorbing compound of formula (I) could then have more than one pair of enantiomers. However, the compound should preferably have a 60/40 to 40/60 (preferably 50/50) ratio of at least two enantiomers (although it can have, for example a 60/40 to 40/60 ratio of enantiomers in each of two sets of enantiomers).

Preferably, none of the carbon atoms of A* is unsaturated, except when A* contains a carbonyl carbon atom or an aryl or heteroaryl group.

It should be noted that UV absorbing compounds are specifically contemplated which are of formula (I) and all the specific examples below. Examples of compounds of the present invention are shown below in Table 1 representing specific formula (Ic).

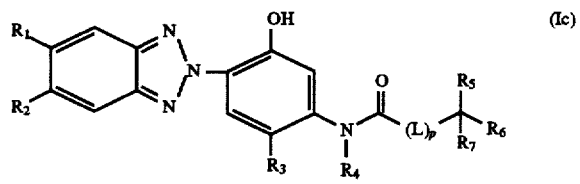

TABLE 1

| $R_1$ | $R_2$ | $R_3$ | $R_4$ | L | $R_5$ | $R_6$ | $R_7$ | Remark |
|---|---|---|---|---|---|---|---|---|
| H | H | $CH_3$ | $CH_3$ | None | H | $CH_3$ | $C_2H_5$ | UV-1 |
| H | H | $CH_3$ | $C_2H_5$ | None | H | $CH_3$ | $C_2H_5$ | UV-2 |
| H | H | $CH_3$ | $C_2H_5$ | None | H | $C_2H_5$ | n-$C_4H_9$ | UV-3 |
| Cl | Cl | H | $C_2H_5$ | None | H | $C_2H_5$ | n-$C_4H_9$ | UV-4 |
| F | F | H | $C_2H_5$ | None | H | $C_2H_5$ | n-$C_4H_9$ | UV-5 |
| H | Cl | $CH_3$ | $C_2H_5$ | None | H | $C_2H_5$ | n-$C_4H_9$ | UV-6 |
| H | Cl | $CH_3$ | $C_2H_5$ | None | H | $C_2H_5$ | n-$C_4H_9$ | UV-7 |
| H | Cl | $CH_3$ | $C_2F_5$ | None | H | $C_2H_5$ | n-$C_4H_9$ | UV-8 |
| H | Cl | $CH_3$ | $C_2H_5$ | None | H | $CH_3$ | $C_2H_5$ | UV-9 |
| Br | Br | H | $C_2H_5$ | None | H | $C_2H_5$ | n-$C_4H_9$ | UV-10 |
| $CH_3O$ | $CH_3O$ | $CH_3$ | $C_2H_5$ | None | H | $C_2H_5$ | n-$C_4H_9$ | UV-11 |
| H | $CH_3O$ | $CH_3$ | $C_2H_5$ | None | H | $C_2H_5$ | n-$C_4H_9$ | UV-12 |
| H | Cl | $CH_3$ | $C_2H_5$ | None | H | $CH_3$ | n-$C_4H_9$ | UV-13 |
| H | H | $CH_3$ | $CH_3$ | $CH_2$ | H | $CH_3$ | $C_2H_5$ | UV-14 |

TABLE 1-continued

| $R_1$ | $R_2$ | $R_3$ | $R_4$ | L | $R_5$ | $R_6$ | $R_7$ | Remark |
|---|---|---|---|---|---|---|---|---|
| H | H | $CH_3$ | $C_2H_5$ | $CH_2$ | H | $CH_3$ | $C_2H_5$ | UV-14 |
| H | H | $CH_3$ | $C_2H_5$ | $CH_2$ | H | $C_2H_5$ | n-$C_4H_9$ | UV-15 |
| Cl | Cl | H | $C_2H_5$ | $CH_2$ | H | $C_2H_5$ | n-$C_4H_9$ | UV-16 |
| F | F | H | $C_2H_5$ | $CH_2$ | H | $C_2H_5$ | n-$C_4H_9$ | UV-17 |
| H | Cl | $CH_3$ | $C_2H_5$ | $CH_2$ | H | $C_2H_5$ | n-$C_4H_9$ | UV-18 |
| H | Cl | $CH_3$ | $C_2H_5$ | $CH_2$ | H | $CH_3$ | $C_2H_5$ | UV-19 |
| Br | Br | H | $C_2H_5$ | $CH_2$ | H | $C_2H_5$ | n-$C_4H_9$ | UV-20 |
| $CH_3O$ | $CH_3O$ | $CH_3$ | $C_2H_5$ | $CH_2$ | H | $C_2H_5$ | n-$C_4H_9$ | UV-21 |
| H | $CH_3O$ | $CH_3$ | $C_2H_5$ | $CH_2$ | H | $C_2H_5$ | n-$C_4H_9$ | UV-22 |
| H | Cl | $CH_3$ | $C_2H_5$ | $CH_2$ | H | $CH_3$ | n-$C_4H_9$ | UV-23 |
| H | H | $CH_3$ | $CH_3$ | None | $CH_3$ | $C_2H_5$ | n-$C_3H_7$ | UV-24 |
| H | H | $CH_3$ | $C_2H_5$ | None | $CH_3$ | $C_2H_5$ | n-$C_3H_7$ | UV-25 |
| H | H | $CH_3$ | $C_2H_5$ | None | $CH_3$ | $C_2H_5$ | n-$C_3H_7$ | UV-26 |
| Cl | Cl | H | $C_2H_5$ | None | $CH_3$ | $C_2H_5$ | n-$C_3H_7$ | UV-27 |
| F | F | H | $C_2H_5$ | None | $CH_3$ | $C_2H_5$ | n-$C_3H_7$ | UV-28 |
| H | Cl | $CH_3$ | $C_2H_5$ | None | $CH_3$ | $C_2H_5$ | n-$C_3H_7$ | UV-29 |
| H | Cl | $CH_3$ | $C_2H_5$ | None | $CH_3$ | $C_2H_5$ | n-$C_3H_7$ | UV-30 |
| Br | Br | H | $C_2H_5$ | None | $CH_3$ | $C_2H_5$ | n-$C_3H_7$ | UV-31 |
| $CH_3O$ | $CH_3O$ | $CH_3$ | $C_2H_5$ | None | $CH_3$ | $C_2H_5$ | n-$C_3H_7$ | UV-32 |
| H | $CH_3O$ | $CH_3$ | $C_2H_5$ | None | $CH_3$ | $C_2H_5$ | n-$C_3H_7$ | UV-33 |

UV absorbing compounds of formula (I) can be prepared from the chromophore of formula (III), below. The compounds of formula (III) can be readily synthesized from inexpensively available starting materials such as o-nitroaniline, 4-chloro-2-nitroaniline and m-aminoalkyl substituted phenols by analogous procedures known in the art (See, for example, U.S. Pat. No. 3,813,255 and FR 1,324,898). For example, the 2-(2'-hydroxy-4'-ethylaminophenyl)benzotriazole can be made by reacting 2-nitrobenzenediazonium chloride with 3-ethylaminophenol followed by reductive ring closure of the azo dye to the desired benzotriazole. Further compounds of formula (I) can be prepared in an analogous manner. It will be understood in each example below, that one of the starting reagents (for example, the alkylcarbonyl chloride) is the corresponding enantiomeric mixture (preferably, a 40/60 to 60/40 enantiomeric mixture). The comparative tert-amido compounds $C_2$-$C_5$ were also made from formula (III) following analogous procedure described in FR 1,324,898, the entire disclosures of which are incorporated herein by reference.

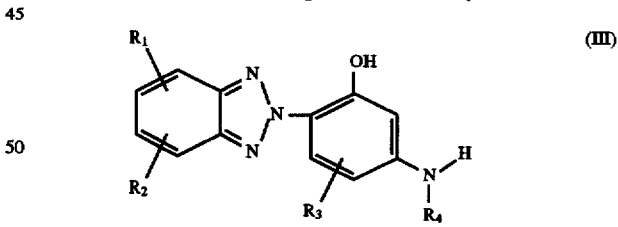

Table 2 illustrates specific examples of the present invention prepared as described above.

TABLE 2

| Example | Compound | Solid (m.p. °C.) or liquid | Compound No. |
|---|---|---|---|
| Comparison | 5-chloro-2H-benzotriazole with 2-hydroxy-5-(N-ethyl-N-acetylamino)phenyl | 169–170 | C-2 |
| Comparison | 5,6-dichloro-2H-benzotriazole with 2-hydroxy-5-(N-ethyl-N-acetylamino)phenyl | 183–184 | C-3 |
| Comparison | 2H-benzotriazole with 2-hydroxy-4-methyl-5-(N-ethyl-N-acetylamino)phenyl | 147–148 | C-4 |
| Comparison | 5-chloro-2H-benzotriazole with 2-hydroxy-4-methyl-5-(N-ethyl-N-acetylamino)phenyl | 127–128 | C-5 |
| Comparison | 2H-benzotriazole with 2-hydroxy-4-methyl-5-(N-ethyl-N-butanoylamino)phenyl | 108–109 | C-6 |
| Comparison | 2H-benzotriazole with 2-hydroxy-4-methyl-5-(N-ethyl-N-(3-methylbutanoyl)amino)phenyl | 118–119 | C-7 |
| Comparison | 5-chloro-2H-benzotriazole with 2-hydroxy-4-methyl-5-(N-ethyl-N-octanoylamino)phenyl | Liquid | C-8 |

TABLE 2-continued

| Example | Compound | Solid (m.p. °C.) or liquid | Compound No. |
|---|---|---|---|
| Invention | [benzotriazole structure with Cl, OH, CH3, C2H5, and branched alkyl chain with H3C groups] | Liquid | I-1 |
| Invention | [benzotriazole structure with OH, CH3, C2H5, and branched alkyl chain with H3C and CH3 groups] | 80–82 | I-2 |

Photographic elements according to the present invention will typically have at least one light sensitive silver halide emulsion layer and a non-light sensitive layer, with the ultraviolet absorbing compound of formula (I) being typically (but not necessarily) located in the non-light sensitive layer. More preferably, a photographic element of the present invention will have the non-light sensitive layer containing the ultraviolet absorbing compound located above all light sensitive layers. However, it is also contemplated that the ultraviolet absorbing compound can additionally be present in another layer, such as an interlayer (or even a light sensitive layer), particularly an interlayer located between red and green sensitive layers in an element having blue, green and red-sensitive layers coated in that order, on a support (particularly a paper support). Any layer of the photographic element in which the UV absorbing compounds of formula (I) are located will normally be a gel layer, and the UV absorbing compound may particularly be dispersed therein using a coupler solvent with or without additional auxilliary solvents such as ethyl acetate.

The UV absorbing compounds can be directly dispersed in the element or dispersed therein in droplets of a solvent dispersion. Alternatively, the UV absorbing compounds of formula (I) can be loaded into a polymer latex by themselves or with other compounds such as high boiling point organic solvents or monomeric UV absorbing compounds. "Loading" a polymer latex is generally described in U.S. Pat. No. 4,199,363 for example. Loading of a polymer latex is also described, for example, in U.S. Pat. No. 4,203,716, U.S. Pat. No. 4,214,047, U.S. Pat. No. 4,247,627, U.S. Pat. No. 4,497,929 and U.S. Pat. No. 4,608,424.

As described, UV absorbing compounds of the present invention are preferably used by themselves in a photographic element. However, they may be used in conjunction with other UV absorbing compounds if desired, such as other benzotriazole based UV absorbers. Examples of such conventional UV absorbing agents which can be used include: 2-(2-hydroxy-5-methylphenyl)-2H-benzotriazole, 2-(2-hydroxy-3,5-di-tert-butylphenyl)-2H-benzotriazole, 2-(2-hydroxy-3-tert-butyl-5-methylphenyl)-2H-benzotriazole, 2-(2-hydroxy-3,5-di-tert-butylphenyl)-5-chloro-2H-benzotriazole, 2-(2-hydroxy-3,5-di-tert-amylphenyl)-2H-benzotriazole, 2-(2-hydroxy-3,5-di(1,1-dimethylbenzyl)-phenyl)-2H-benzotriazole, 2-(2-hydroxy-5-tert-octylphenyl)-2H-benzotriazole, and those described in U.S. Pat. No. 5,500,332 and commonly assigned allowed U.S. patent application Ser. No. 08/346,717 filed Nov. 30, 1994 and commonly assigned U.S. patent application Ser. No. 08/624,328 filed Mar. 29, 1996, the disclosures of which are incorporated herein by reference. Other types of UV absorbing agents such as p-hydroxybenzoates, phenylesters of benzoic acid, salicylanilides and oxanilides, diketones, benzylidene malonate, esters of α-cyano-cinnamic acid, and organic metal photostabilizers, and others, as described in J. F. Rabek, *Photostabilization of Polymers, Principles and Applications*, Elsevier Science Publishers LTD, England, page 202–278(1990).

The UV absorbing compound is incorporated into the photographic element, typically into a gelatin dispersion in an amount of between 0.2 g/m$^2$ to 10 g/m$^2$, and more preferably between 0.5 g/m$^2$ to 5.0 g/m$^2$. Furthermore, when incorporated as a solvent dispersion using a water immiscible organic solvent, the weight ratio of high boiling, water immiscible organic solvent to UV absorbing compound is preferably between 0.1 to 5.0 (that is, 0.1/1 to 5.0/1 of solvent/UV absorbing compound), and more preferably between 0.2 to 3.0 (that is, 0.2/1 to 3.0/1 of solvent/UV absorbing compound).

The UV absorbing compound of formula (I) is provided in any one or more of the layers (for example, a hydrophilic colloid layer such as a gelatin layer) of a photographic light-sensitive material (for example, a silver halide photographic light-sensitive material), such as a surface protective layer, an intermediate layer or a silver halide emulsion layer, and the like. For example, in photographic paper the UV absorbing compound of formula (I) with/without other UV absorbing compounds, may be positioned above and/or below the red sensitive layer (typically adjacent to it), the red sensitive layer typically being the uppermost light sensitive layer in color paper, or even completely or partially within the red sensitive layer. The UV absorbing compound is typically provided in a given layer of a photographic element by coating the hydrophilic colloid material (such as a gelatin emulsion) which contains the latex, onto a support or another previously coated layer forming part of the element.

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support).

Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. No. 4,279,945 and U.S. Pat. No. 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to *Research Disclosure*, September 1996, Number 389, Item 38957, which will be identified hereafter by the term "Research Disclosure I." The Sections hereafter referred to are Sections of the Research Disclosure I unless otherwise indicated. All Research Disclosures referenced herein are published by Kenneth Mason Publications, Ltd., Dudley Annex, 12a North Street, Emsworth, Hampshire PO10 7DQ, ENGLAND. The foregoing references and all other references cited in this application, are incorporated herein by reference.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through V. Color materials and development modifiers are described in Sections V through XX. Vehicles which can be used in the elements of the present invention are described in Section II, and various additives such as brighteners, antifoggants, stabilizers, light absorbing and scattering materials, hardeners, coating aids, plasticizers, lubricants and matting agents are described, for example, in Sections VI through X and XI through XIV. Manufacturing methods are described in all of the sections, other layers and supports in Sections XI and XIV, processing methods and agents in Sections XIX and XX, and exposure alternatives in Section XVI.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. No. 4,163,669; U.S. Pat. No. 4,865,956; and U.S. Pat. No. 4,923,784 are particularly useful. Also contemplated is the use of nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019, 492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612;. 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. This reference and all other references cited in this application are incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. No. 4,346,165; U.S. Pat. No. 4,540,653 and U.S. Pat. No. 4,906,559); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in the elements of the invention are disclosed in Japanese Published Applications 83-09,959; 83-62,586; 90-072,629, 90-072,630; 90-072,632; 90-072,633; 90-072,634; 90-077,822; 90-078,229; 90-078,230; 90-079,336; 90-079,338; 90-079,690; 90-079,691; 90-080,487; 90-080,489; 90-080,490; 90-080,491; 90-080,492; 90-080,494; 90-085,928; 90-086,669; 90-086,670; 90-087,361; 90-087,362; 90-087,363; 90-087,364; 90-088,096; 90-088,097; 90-093,662; 90-093,663; 90-093,664; 90-093,665; 90-093,666; 90-093,668; 90-094,055; 90-094,056; 90-101,937; 90-103,409; 90-151,577.

The silver halide used in the photographic elements may be silver iodobromide, silver bromide, silver chloride, silver chlorobromide, silver chloroiodobromide, and the like. For example, the silver halide used in the photographic elements of the present invention may contain at least 90% silver chloride or more (for example, at least 95%, 98%, 99% or 100% silver chloride). In the case of such high chloride silver halide emulsions, some silver bromide may be present but typically substantially no silver iodide. Substantially no silver iodide means the iodide concentration would be no more than 1%, and preferably less than 0.5 or 0.1%. In particular, in such a case the possibility is also contemplated that the silver chloride could be treated with a bromide source to increase its sensitivity, although the bulk concentration of bromide in the resulting emulsion will typically be no more than about 2 to 2.5% and preferably between about 0.6 to 1.2% (the remainder being silver chloride). The foregoing % figures are mole %.

The type of silver halide grains preferably include polymorphic, cubic, and octahedral. The grain size of the silver halide may have any distribution known to be useful in photographic compositions, and may be ether polydipersed or monodispersed.

Tabular grain silver halide emulsions may also be used. Tabular grains are those with two parallel major faces each clearly larger than any remaining grain face and tabular grain emulsions are those in which the tabular grains account for at least 30 percent, more typically at least 50 percent, preferably>70 percent and optimally>90 percent of the total grain projected area. The tabular grains can account for substantially all (>97 percent) of the total grain projected area. The tabular grain emulsions can be high aspect ratio tabular grain emulsions - - - i.e., ECD/t>8, where ECD is the diameter of a circle having an area equal to the grain projected area and t is the tabular grain thickness; intermediate aspect ratio tabular grain emulsions - - - i.e., ECD/t=5 to 8; or low aspect ratio tabular grain emulsions - - - i.e., ECD/t=2 to 5. The emulsions typically exhibit high tabularity (T), where T (i.e., $ECD/t^2$)>25 and ECD and t are both measured in micrometers (μm). The tabular grains can be of any thickness compatible with achieving an aim average aspect ratio and/or average tabularity of the tabular grain emulsion. Preferably the tabular grains satisfying projected area requirements are those having thicknesses of<0.3 μm, thin (<0.2 μm) tabular grains being specifically preferred and ultrathin (<0.07 μm) tabular grains being contemplated for maximum tabular grain performance enhancements. When the native blue absorption of iodohalide tabular grains is relied upon for blue speed, thicker tabular grains, typically up to 0.5 μm in thickness, are contemplated.

High iodide tabular grain emulsions are illustrated by House U.S. Pat. No. 4,490,458, Maskasky U.S. Pat. No. 4,459,353 and Yagi et al EPO 0 410 410.

Tabular grains formed of silver halide(s) that form a face centered cubic (rock salt type) crystal lattice structure can have either {100} or {111} major faces. Emulsions containing {111} major face tabular grains, including those with controlled grain dispersities, halide distributions, twin plane spacing, edge structures and grain dislocations as well as adsorbed {111} grain face stabilizers, are illustrated in those references cited in *Research Disclosure I*, Section I.B.(3) (page 503).

The silver halide grains to be used in the invention may be prepared according to methods known in the art, such as those described in *Research Disclosure I* and James, *The Theory of the Photographic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, rhodium, ruthenium, phosphorous, or combinations thereof. Chemical sensitization is generally carried out at pAg levels of from 5 to 10, pH levels of from 5 to 8, and temperatures of from 30° to 80° C., as illustrated in *Research Disclosure I*, Section IV (pages 510–511) and the references cited therein.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or in an alcohol. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, New York, 1977. In the case of processing a reversal color element, the element is first treated with a black and white developer followed by treatment with a color developer to produce a positive dye image. The negative color element, the first developer is a color developer so as to produce a negative dye image. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(β-(methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Development is followed by bleach-fixing, to remove silver or silver halide, washing and drying.

The present invention will be further described in the examples below which illustrate UV absorbing compounds and photographic elements of this invention.

EXAMPLES

For making compounds described in Table 2, 2-(2'-hydroxy-4'-aminoethylphenyl)benzotriazole derivatives were required. These were synthesized by reduction of the corresponding acetamido-substituted compound with alane in about 90% yield by similar procedure known in the art (see, for example, Lal C. Vishwakarma et al, *Heterocycles*, 19, 1453 (1982)).

Properties of the UV Absorbers of the Present Invention

Physical properties, including optical absorption profiles were measured for various of the compounds of the present invention, as well as comparative compounds, as shown in Table 3 below. In Table 3, $\lambda_{max}$ is the wavelength of maximum absorption (measured in MeOH as indicated in the Table), $\epsilon_{max}$ is the extinction coefficient, and the half bandwidth is the width of the absorption peak centered about $\lambda_{max}$ as measured at one-half the maximum absorption $\lambda_{max}$. All of the foregoing were measured in methanol. The percent yields of the products are not optimized.

TABLE 3

| Example No. | % Yield | $\lambda_{max}$ (nm) (in MeOH) | $\epsilon_{max}$ (×10⁴) | Half Band width (nm) | Remark |
|---|---|---|---|---|---|
| C-1 (II-A/II-B) | — | 342 | 1.57 | 86 | Solid |
| C-2 | 64 | 338 | 2.24 | 68 | Solid |
| C-3 | 58 | 344 | 2.24 | 68 | Solid |
| C-4 | 94 | 336 | 1.90 | 68 | Solid |
| C-5 | 90 | 342 | 2.02 | 68 | Solid |
| C-6 | 87 | 337 | 1.96 | 68 | Solid |
| C-7 | 90 | 336 | 1.90 | 68 | Solid |
| C-8 | 98 | 342 | 2.00 | 68 | Liquid |
| I-1 | 86 | 342 | 2.00 | 68 | Liquid |
| I-2 | 88 | 337 | 1.99 | 68 | Solid |

The comparative examples C-1 through C-8 in Table 3 are lacking asymmetric carbon center.

Table 1 illustrates the higher melting character of the comparative examples related to prior art. As a result, they are prone to crystallize out in the dispersion and/or coating even if they have racemic chains particularly in primary carboxamido substituted compounds. As shown below, in Table 4 the comparative examples, if solid, are prone to crystallize out in the dispersion and/or coating. If these happen to be liquid, their intrinsic light stability is quite inferior.

Photographic Evaluation 1.45 g of UV absorber was dissolved at elevated temperature (50°–70° C.) in 480 mg of 1,4-cyclohexylenedimethylene bis-(2-ethylhexanoate) and, if UV absorber was a solid at room temperature, an additional 4.35 g of ethyl acetate was used. This oil phase was added with high shear stirring to a 70° C. aqueous gelatin solution (containing per liter 40.1 g of gelatin and 31.0 mL of 10% aqueous Alkanol - XC) and passed five times through a colloid mill for adequate particle size reduction. The dispersion is inspected microscopically for general particle size and crystallinity, and coated about $0.108 \times 10^{-4}$ moles/m² on an acetate base in a two layer SOC-type format, allowed to dry and the coating is also inspected microscopically for crystallinity (See Table 4). Fresh coated spectral absorption data are recorded using a Perkin-Elmer Lambda 4C High Performance UV-VIS Spectrophotometer, and coated samples are HID (50 Klux Daylight; 315–700 nm) and HIS (50 Klux Sunshine; 280–700 nm) tested and compared to fresh data in order to obtain UV absorber intrinsic light stability information. (For HID and HIS explanation, see Lewis R. Koller, *Ultraviolet Radiation*, John Wiley & Sons, Inc., N.Y., N.Y., 1965).

Absorption spectra for various of the compounds were obtained in methanolic solution (Table 3). Absorption spectra from fresh coatings were obtained as described below and shown in FIG. 1. In particular, FIG. 1 shows the absorption spectra in coating for inventive compound I-1 and the control compounds C-1 (II-A/II-B) in total transmission (TT) mode of the spectrophotometer. Note from FIG. 1 that inventive UV absorbing compound I-1 (shown by dashed line) exhibits, in addition to a steeper slope at its longer wavelengths of absorption (that is, near 380 nm) and a particular drop-off to a lower absorption at their longest wavelength of the absorption, a higher extinction coefficient than comparative control compounds C-1(II-A/II-B)(solid line) as measured from fresh coating of their respective dispersions.

Microscopic observations for crystallinity in experimental UV absorber dispersions and coatings of these materials and their absorption spectra were performed as described here. Microscopy is undertaken in the preparation of dispersions of experimental materials in order to provide an initial indication of physical properties such as general particle size and stability (that is, tendency to crystallize). The microscopic particle size characterizations are performed using oil immersion optics −1000x microscopy, and −200x cross-polarized microscopy is used for crystal characterization. Microscopic evaluation of the coatings is also undertaken because an acceptable non-crystalline dispersion may recrystallize in the coated format. Assuming there are no recrystallization problems, duplicate samples are spectrophotometrically measured using a Perkin-Elmer High Performance Lambda 4C spectrometer. These samples are then submitted for two Week HID and HIS light stability testing, and the post-testing spectra is measured and compared to the fresh measurements in order to determine intrinsic light stability of the UV absorber. Since the experimental dispersion formulation used for these experiments is common and only optimized from the standpoint of low melting solids and its beneficial effect on dispersion crystallinity, coated spectroscopy data are obtained primarily using the total transmission mode of operation where an integrating sphere is used in the spectrophotometer. This has the effect of diminishing light scattering effects due to particle size, so misleading extinction differences caused by light scattering in the specular mode can be overlooked.

A microscopic check for crystal formation from the above procedure, yielded the results in Table 4 below:

TABLE 4

| Tendency to Form Undesirable Crystals | | | |
|---|---|---|---|
| Compound No. | Example No. | Dispersion | Coating |
| I-1 | Invention | A liquid | A liquid |
| I-2 | Invention | It did not crystallize | It did not crystallize |
| C-1 (II-AAI-B) | Comparison | — | — |
| C-2 | Comparison | Crystallized | Crystallized |
| C-3 | Comparison | Crystallized | Crystallized |
| C-4 | Comparison | Crystallized | Crystallized |
| C-5 | Comparison | Crystallized | Crystallized |
| C-6 | Comparison | Crystallized | Crystallized |
| C-7 | Comparison | Crystallized | Crystallized |

TABLE 4-continued

| Tendency to Form Undesirable Crystals | | | |
|---|---|---|---|
| Compound No. | Example No. | Dispersion | Coating |
| C-8 | Comparison | A liquid | A liquid |

Table 4 illustrates how UV absorbing compound I-2 of the present invention did not form any detectable crystals either in dispersion or in coating. On the other hand, the comparison compounds C-6 and C-7 being an exact match of invention compound I-2 in terms of number of atoms and position of amido group attachment in the hydroxyphenyl ring, but lacking a racemic carbon center crystallized out in the coatings. This observation clearly illustrates the superiority of asymmetric carbon containing UV absorbing solid compounds of formula (I). Incidentally, whenever some UV absorbing compounds, such as example C-8, become liquids their intrinsic light stability often is inferior as will be illustrated in Table 5.

Intrinsic light stability data for UV absorbing compounds of this invention are summarized in Table 5. A combination of the compounds II-A & II-B has been used as a Control in each coating set and is referred to as C-1. The optical density loss, relative to the control coatings, was measured at 350 nm from coating spectral data.

TABLE 5

| | Light Stability | | | |
|---|---|---|---|---|
| Sample No. | 2 Week HID | 4 Week HID | 2 Week HIS | 4 Week HIS |
| C-1 (II-A/II-B) | −8.63 | −11.47 | −8.70 | −16.18 |
| C-7 | −7.44 | −13.77 | −8.08 | −24.91 |
| C-8 | −4.35 | −14.26 | −5.87 | −27.69 |
| I-1 | −2.08 | −6.53 | −1.51 | −14.10 |
| I-2 | −5.37 | −10.73 | −4.28 | −19.56 |

The intrinsic light stability data from Table 5 clearly illustrate that the inventive compound I-1 is better than the control compounds II-A/II-B (C-1) and particularly better than its exact match C-8 while C-8 and I-1 both being liquid compounds. Also, the invention compound I-2 containing an asymmetric carbon atom is far superior to its non-racemic exact match version C-7 in terms of light stability and no crystal forming tendency as shown in Table 4. Most preferred UV absorbing compounds of this invention are I-1 and I-1 based, nonetheless I-2 and I-2 based compounds are photographically important as well. The data from Table 5 suggest that the presence of asymmetric carbon center seems to enhance intrinsic light stability of the UV absorbing compounds of this invention.

The present invention also specifically contemplates multilayer photographic elements as described in *Research Disclosure*, February 1995, Item 37038 (pages 79–115). Particularly contemplated is the use of any of the enantiomeric mixtures of formula (I) (particularly a 50/50 mixture of the two enantiomers) in such elements. Particularly, a 50/50 enantiomeric mixture of any one of the compounds of this invention may be used as the UV absorbing compound in an overcoat of each of the photographic elements described in detail in Sections XVII through XXII of that *Research Disclosure*.

The preceding examples are set forth to illustrate specific embodiments of this invention and are not intended to limit the scope of the compositions or materials of the invention. It will be understood that variations and modifications can be effected within the spirit and scope of the invention.

We claim:

1. A photographic element comprising an ultraviolet absorbing compound of the following structure:

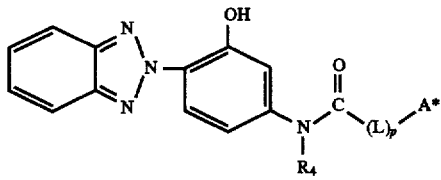
(I)

wherein:

R₄ is a substituted or unsubstituted alkyl group, R₄ may be further joined to either L or A* forming a ring and the benzo or phenyl ring shown may be further substituted or unsubstituted;

L is a bivalent linking group;

p is 0 or 1;

A* is an alkyl group having an asymmetric carbon or asymmetric silicon atom, and;

wherein the ultraviolet absorbing compound of formula (I) is a mixture of two enantiomers about the asymmetric carbon or silicon atom of A*.

2. A photographic element according to claim 1, wherein p is 1 and L is an alkylene group having a chain of 1 to 20 atoms in length, with or without intervening oxygen, sulfur or nitrogen atoms; an aryl group; or a saturated or unsaturated heterocyclic group.

3. A photographic element according to claim 2, wherein L is an alkylene group containing at least one intervening oxygen, sulfur or nitrogen atom.

4. A photographic element according to claim 1, wherein R₄, is an alkyl group substituted with an alkoxy, halogen or cyano group.

5. A photographic element according to claim 1, wherein R₄ is a perfluoroalkyl group.

6. A photographic element according to claim 1, wherein the ultraviolet absorbing compound is a 60/40 to 40/60 mixture of two enantiomers.

7. A photographic element according to claim 1, the element additionally comprising at least one light sensitive silver halide emulsion layer and a non-light sensitive layer, wherein the ultraviolet absorbing compound is located in the non-light sensitive layer.

8. A photographic element according to claim 7, wherein the non-light sensitive layer containing the ultraviolet absorbing compound is located above all light sensitive layers.

9. A photographic element according to claim 1, additionally comprising a reflective support and at least one silver halide emulsion layer, and wherein the ultraviolet absorbing compound is located in the silver halide emulsion layer or in a layer positioned further from the support than the silver halide emulsion layer.

10. A photographic element according to claim 9, additionally comprising a fluorescent brightener.

11. A photographic element according to claim 9, wherein the fluorescent brightener absorbs ultraviolet in the 350–410 nm range in order to fluoresce in the range of 400–500 nm.

12. A photographic element according to claim 1, wherein the ultraviolet absorbing compound is present in an amount of between 0.2 g/m² to 10 g/m².

13. A photographic element according to claim 1, wherein the ultraviolet absorbing compound is of formula (Ia):

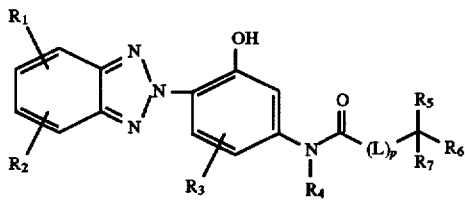
(Ia)

wherein:

R₁ or R₂ independently represent alkyl group, alkoxy group, aryl group, heteroaryl group, or aryloxy group, and the alkyl or alkoxy may contain from 1 to 5 intervening oxygen, sulfur or nitrogen atoms, or any of R₁, R₂ or R₃ is H, cyano or a halogen atom, or both R₁ and R₂ together form an aromatic group or hetero aromatic group, or R₃ can additionally be H or 6'-hydroxy, or 5'-H or an alkyl group;

R₄ an alkyl group or perfluoroalkyl group;

L is a bivalent linking group;

p is 0 or 1; and

R₅, R₆ and R₇ are, independently: H; halogen; cyano; an alkyl group or alkoxy group; thioalkyl group; alkylamino or arylamino group; an aryl group or aryloxy group; or a heteroaryl group;

provided that R₅, R₆, and R₇ are selected such that the carbon atom to which they are attached is asymmetric;

the ultraviolet absorbing compound being a 60/40 to 40/60 mixture of two enantiomers about the asymmetric carbon of A*.

14. A photographic element according to claim 13, wherein R₅, R₆ and R₇ are each a 1 to 20 carbon atom alkyl group, or H.

15. A photographic element according to claim 14, wherein each of R₁, R₂ and R₃, is an alkyl group, alkoxy group, H or halogen.

16. A photographic element according to claim 13, wherein the ultraviolet absorbing compound of formula (I) is a 50/50 mixture of two enantiomers.

17. A photographic element according to claim 1, the element additionally comprising at least one light sensitive silver halide emulsion layer and a non-light sensitive layer, wherein the ultraviolet absorbing compound is of formula (Ib):

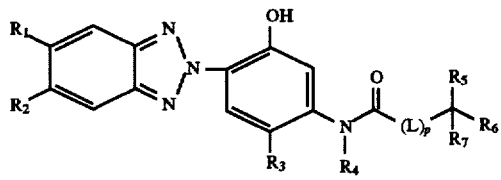
(Ib)

wherein:

R₁ or R₂ independently represent alkyl group, alkoxy group, aryl group, heteroaryl group, or aryloxy group, and the alkyl or alkoxy may contain from 1 to 5 intervening oxygen, sulfur or nitrogen atoms, or any of R₁, R₂ or R₃ is H, cyano or a halogen atom, or both R₁ and R₂ together form an aromatic group or hetero aromatic group, or R₃ can additionally be H or 6'-hydroxy, or 5'-H or an alkyl group;

R₄ a substituted or unsubstituted alkyl group;

L is a bivalent linking group;

p is 0 or 1; and

R₅, R₆ and R₇ are, independently: H; halogen; cyano; an alkyl group or alkoxy group; thioalkyl group; alkylamino or arylamino group; an aryl group or aryloxy group; or a heteroaryl group;

provided that $R_5$, $R_6$, and $R_7$ are selected such that the carbon atom to which they are attached is asymmetric;

the ultraviolet absorbing compound being a 60/40 to 40/60 mixture of two enantiomers about the asymmetric carbon of A*.

18. A photographic element according to claim 17, wherein the ultraviolet absorbing compound is of the formula:

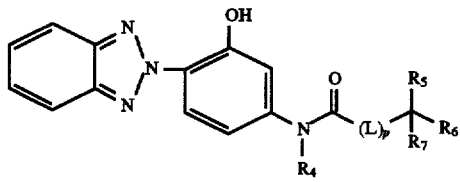

wherein $R_4$, $R_5$, $R_6$, $R_7$, L and p are as defined in claim 16.

19. A photographic element according to claim 18, wherein p is 1.

20. A photographic element according to claim 19, wherein L is a 1 to 10 carbon atom alkylene group.

21. A photographic element according to claim 20, wherein L is a methylene group.

22. A photographic element according to claim 17, wherein $R_4$ is a perfluoro alkyl group.

23. A photographic element according to claim 17, the element additionally comprising at least one light sensitive silver halide emulsion layer and a non-light sensitive layer, wherein the ultraviolet absorbing compound is located in the non-light sensitive layer.

24. A photographic element according to claim 17, wherein the non-light sensitive layer containing the ultraviolet absorbing compound is located above all light sensitive layers.

25. A photographic element according to claim 17, additionally comprising a reflective support and at least one silver halide emulsion layer, and wherein the ultraviolet absorbing compound is located in the silver halide emulsion layer or in a layer positioned further from the support than the silver halide emulsion layer.

* * * * *